(12) United States Patent
Mishra et al.

(10) Patent No.: US 9,440,071 B2
(45) Date of Patent: Sep. 13, 2016

(54) SYSTEMS AND METHODS FOR FACILITATING BINAURAL HEARING BY A COCHLEAR IMPLANT PATIENT

(75) Inventors: Lakshmi N. Mishra, Valencia, CA (US); Leonid M. Litvak, Los Angeles, CA (US); Abhijit Kulkarni, Newbury Park, CA (US); Lee F. Hartley, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 175 days.

(21) Appl. No.: 14/360,587

(22) PCT Filed: Dec. 29, 2011

(86) PCT No.: PCT/US2011/067891
§ 371 (c)(1),
(2), (4) Date: May 23, 2014

(87) PCT Pub. No.: WO2013/101088
PCT Pub. Date: Jul. 4, 2013

(65) Prior Publication Data
US 2014/0330344 A1 Nov. 6, 2014

(51) Int. Cl.
*H04R 25/00* (2006.01)
*A61N 1/36* (2006.01)
*A61N 1/05* (2006.01)

(52) U.S. Cl.
CPC ........... *A61N 1/36032* (2013.01); *H04R 25/30* (2013.01); *H04R 25/43* (2013.01); *H04R 25/552* (2013.01); *A61N 1/0541* (2013.01)

(58) Field of Classification Search
CPC ............ H04R 25/606; H04R 2225/67; A61F 2002/183; A61F 2/18; A61N 1/36032
USPC ................ 600/25; 607/55, 57; 381/312, 320
See application file for complete search history.

(56) References Cited

U.S. PATENT DOCUMENTS 7,174,214 B2    2/2007  Seligman
2009/0012783 A1  1/2009  Klein
(Continued)

FOREIGN PATENT DOCUMENTS

EP          0349599      12/1995
EP          2360943       8/2011
WO      WO-2010/022456    3/2010

OTHER PUBLICATIONS

International Search Report and Written Opinion received in International Application No. PCT/US11/067891, dated Jul. 20, 2012.

*Primary Examiner* — Brian Ensey
(74) *Attorney, Agent, or Firm* — ALG Intellectual Property, LLC

(57) ABSTRACT

An exemplary system for facilitating binaural hearing by a cochlear implant patient includes 1) a spectral analysis facility configured to divide a first audio signal presented to a first ear of the patient and a second audio signal presented to a second ear of the patient into first and second sets of analysis channels, respectively, and 2) a processing facility configured to process acoustic content contained in a first analysis channel included in the first set of analysis channels and acoustic content contained in a second analysis channel included in the second set of analysis channels, mix the processed acoustic content contained in the first and second analysis channels, and direct a cochlear implant to apply electrical stimulation representative of the mixed acoustic content to the first ear by way of a stimulation channel that corresponds to the first analysis channel.

25 Claims, 14 Drawing Sheets

(56) References Cited

U.S. PATENT DOCUMENTS

| | | |
|---|---|---|
| 2009/0220107 A1 | 9/2009 | Every et al. |
| 2010/0172506 A1 | 7/2010 | Iwano |
| 2010/0195836 A1 | 8/2010 | Platz |
| 2010/0312308 A1 | 12/2010 | Busby |
| 2011/0064241 A1* | 3/2011 | Kulkarni ............ A61N 1/36032 381/94.2 |
| 2011/0125218 A1 | 5/2011 | Busby |
| 2011/0293108 A1* | 12/2011 | Mejia ................... H04R 25/407 381/92 |
| 2011/0307249 A1 | 12/2011 | Kellermann et al. |

* cited by examiner

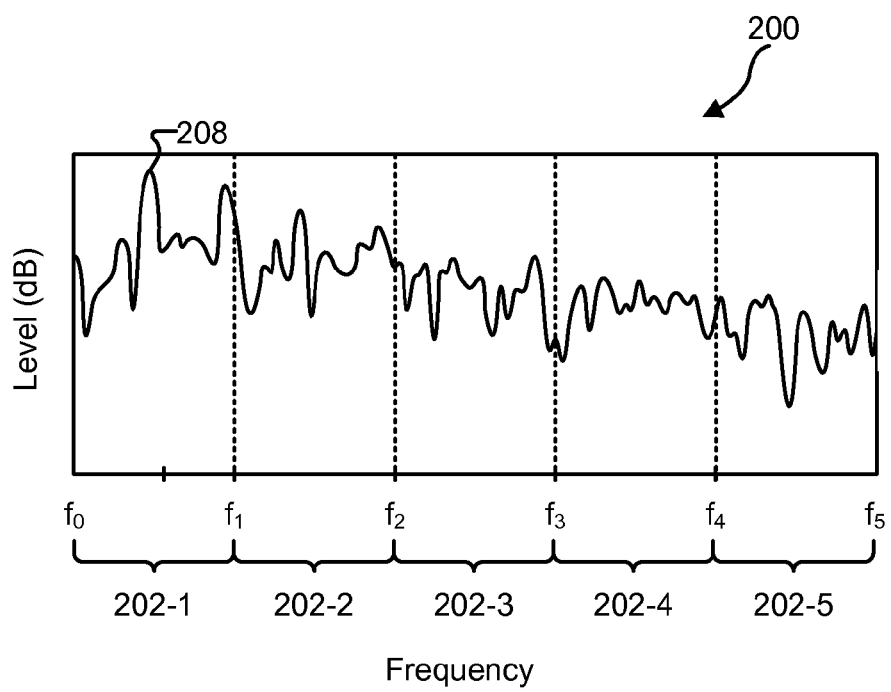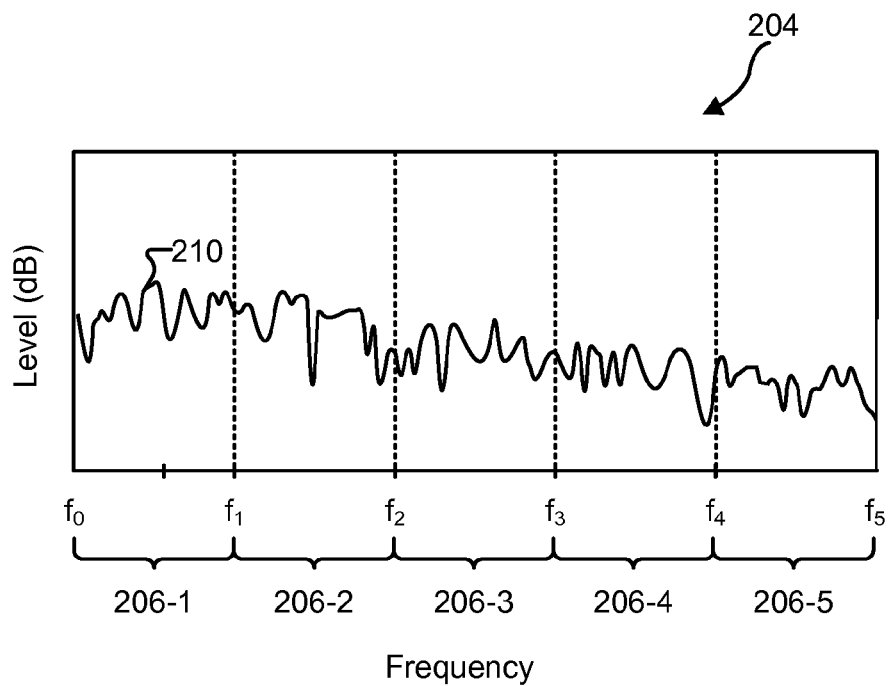
Fig. 2

SYSTEMS AND METHODS FOR FACILITATING BINAURAL HEARING BY A COCHLEAR IMPLANT PATIENT

BACKGROUND INFORMATION

Binaural hearing refers to the use of both ears in order to locate the direction of sound sources. Binaural hearing boosts a person's ability to focus on speech in noisy situations, and allows a person to tune into relatively soft sounds. Unfortunately many cochlear implant patients (i.e., people who have been fitted with a cochlear implant in one or both ears) are incapable of binaural hearing. For example, conventional unilateral cochlear implant systems detect sound provided to only one ear of a patient, thus resulting in the patient being incapable of binaural hearing (assuming that the patient cannot hear with the non-implanted ear). Even some conventional bilateral cochlear implant systems do not provide a full sense of binaural hearing to a patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 shows graphs of first and second audio signals after they have been divided into sets of analysis channels according to principles described herein.

DETAILED DESCRIPTION

Systems and methods for facilitating binaural hearing by a cochlear implant patient are described herein. As will be described below, a sound processing system may 1) divide a first audio signal detected by a first microphone associated with a first ear of a cochlear implant patient into a first set of analysis channels, 2) divide a second audio signal detected by a second microphone associated with a second ear of the patient into a second set of analysis channels corresponding to the first set of analysis channels, 3) process acoustic content contained in a first analysis channel included in the first set of analysis channels and acoustic content contained in a second analysis channel included in the second set of analysis channels, the first and second analysis channels both corresponding to a particular frequency band, 4) mix the processed acoustic content contained in the first and second analysis channels, and 5) direct a cochlear implant to apply electrical stimulation representative of the mixed acoustic content to the first ear by way of a stimulation channel that corresponds to the first analysis channel. Steps three through five may also be performed for each of the other corresponding pairs of analysis channels included in the first and second sets of analysis channels, thus resulting in the first and second audio signals being processed and mixed on a channel-by-channel (i.e., a frequency band-by-band) basis. By so doing, binaural hearing may be facilitated (e.g., for unilateral cochlear implant patients) and/or enhanced (e.g., for bilateral cochlear implant patients).

The channel-by-channel processing and mixing described herein is advantageous compared to conventional approaches used to provide a sense of binaural hearing for cochlear implant patients for a variety of reasons. For example, some conventional approaches compare the first and second audio signals as a whole and select one of them for presentation to the patient based on the comparison. This may prevent the patient from perceiving important information included in the unselected audio signal. In contrast, the channel-by-channel processing and mixing described herein may facilitate conveyance of channel specific information included in each audio signal to the patient, thereby resulting in a more effective and enjoyable binaural hearing experience for the patient.

Figure 1:
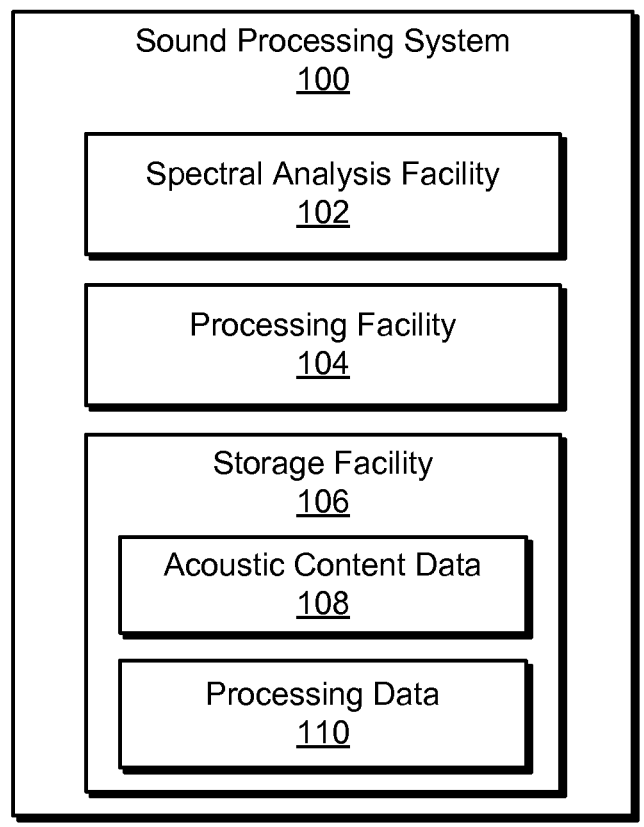
FIG. 1 illustrates an exemplary sound processing system according to principles described herein.

FIG. 1 illustrates an exemplary sound processing system 100 ("system 100"). As shown, system 100 may include, without limitation, a spectral analysis facility 102, a processing facility 104, and a storage facility 106 communicatively coupled to one another. One or more of facilities 102-106 may include one or more computing devices and/or processors configured to perform one or more of the functions described herein. Facilities 102-106 will now be described in more detail.

Spectral analysis facility 102 may be configured to divide a first audio signal detected by first microphone associated with a first ear of a cochlear implant patient into a first set of analysis channels and divide a second audio signal detected by a second microphone associated with a second ear of the patient into a second set of analysis channels. The first and second audio signals may be detected by the first and second microphones in any suitable manner (e.g., concurrently). Exemplary configurations that may be used to detect the first and second audio signals will be described below.

FIG. 2 shows a graph 200 of a first audio signal after it has been divided into a first set of analysis channels 202 (e.g., analysis channels 202-1 through 202-5). FIG. 2 also shows a graph 204 of a second audio signal after it has been divided into a second set of analysis channels 206 (e.g., analysis channels 205-1 through 206-5).

As shown, each analysis channel 202 and 206 may correspond to a particular frequency band. For example, analysis channels 202-1 and 206-1 both correspond to a frequency band defined by frequencies $f_0$ and $f_1$, analysis channels 202-2 and 206-2 both correspond to a frequency band defined by frequencies $f_1$ and $f_2$, etc. As used herein, the term "corresponding analysis channels" refers to analysis channels that correspond to the same frequency band. For example, analysis channels 202-1 and 206-1 are corresponding analysis channels because they both correspond to the frequency band defined by frequencies $f_0$ and $f_1$.

As shown, each analysis channel 202 and 206 may contain acoustic content (e.g., spectral content associated with the first and second audio signals) represented by curves 208 and 210, respectively. While acoustic content is shown to be included in each of the analysis channels 202 and 206 illustrated in FIG. 2, it will be recognized that in some cases, a particular analysis channel may not include any acoustic content.

Spectral analysis facility 102 may divide the first and second audio signals into analysis channels 202 and 206 in any suitable manner. For example, spectral analysis facility 102 may include a plurality of band-pass filters configured to divide the audio signals into a plurality of frequency channels or bands. Additionally or alternatively, spectral analysis facility 102 may be configured to convert the audio signals from a time domain into a frequency domain and then divide the resulting frequency bins into the analysis channels. To this end, spectral analysis facility 102 may apply a Discrete Fourier Transform (e.g., a Fast Fourier Transform ("FFT")) to the audio signals.

Returning to FIG. 1, processing facility 104 may be configured to process and mix the acoustic content contained in each of the corresponding analysis channels associated with the first and second audio signals on a channel-by-channel basis. For example, processing facility 104 may process acoustic content contained in an analysis channel (e.g., analysis channel 202-1) included in the first set of analysis channels and acoustic content contained in a corresponding analysis channel (e.g., analysis channel 206-1) included in the second set of analysis channels. Processing facility 104 may then mix the processed acoustic content contained in the pair of corresponding analysis channels (e.g., analysis channels 202-1 and 206-1). Similar processing may be performed on each of the other pairs of corresponding analysis channels included in the first and second sets of analysis channels.

Various manners in which processing facility 104 may process and mix acoustic content contained in a pair of corresponding analysis channels will now be described. For purposes of the examples provided herein, it will be assumed that the pair of corresponding analysis channels includes a first analysis channel (e.g., analysis channel 202-1) and a second analysis channel (e.g., analysis channel 206-1) that both correspond to the same frequency band.

In some examples, processing facility 104 may process the acoustic content contained in the first and second analysis channels by comparing the acoustic content contained in the first analysis channel with the acoustic content contained in the second analysis channel, applying a gain to the acoustic content contained in the first analysis channel in accordance with the comparison, and applying a gain to the acoustic content contained in the second analysis channel in accordance with the comparison. Processing facility 104 may then generate a mixed signal by summing or otherwise combining the gain-adjusted acoustic content contained in the first and second analysis channels.

Processing facility 104 may compare the acoustic content contained in the first and second analysis channels any suitable manner. For example, processing facility 104 may compare (e.g., determine a difference between) a signal-to-noise ratio of the acoustic content contained in the first analysis channel and a signal-to-noise ratio of the acoustic content contained in the second analysis channel. Processing facility 104 may then determine the gain that is to be applied to the acoustic content contained in the first and second analysis channels based on the difference between the signal-to-noise ratio of the acoustic content contained in the first and second analysis channels. For example, if the acoustic content contained in the first analysis channel has a relatively higher signal-to-noise ratio than the acoustic content contained in the second analysis channel, processing facility 104 may apply a relatively higher gain to the acoustic content contained in the first analysis channel than to the acoustic content contained in the second analysis channel. An example of this will be provided in more detail below.

Additionally or alternatively, processing facility 104 may compare an energy level (e.g., a spectral energy level) of the acoustic content contained in the first analysis channel with an energy level of the acoustic content contained the second analysis channel. Processing facility 104 may then determine the gain that is to be applied to the acoustic content contained in the first and second analysis channels based on the relative energy levels of the acoustic content contained therein. For example, if the acoustic content contained in the first analysis channel has a relatively higher energy level than the acoustic content contained in the second analysis channel, processing facility 104 may apply a relatively higher gain to the acoustic content contained in the first analysis channel than to the acoustic content contained in the second analysis channel.

Additionally or alternatively, processing facility 104 may compare the acoustic content contained in the first and second analysis channels by determining a level of correlation between the acoustic content contained in the first and second analysis channels. This may be performed in any suitable manner. As used herein, "correlation" refers to a degree of similarity between the acoustic content contained in the first and second analysis channels, respectively. If the level of correlation between the acoustic content contained in the first and second analysis channels is relatively high, a relatively similar amount of gain may be applied to the acoustic content contained in both analysis channels so that the acoustic content contained in both analysis channels is presented to the patient. However, if the level of correlation between the acoustic content contained in the first and second analysis channels is relatively low, the amount of gain that is applied to the acoustic content contained in each analysis channel may vary accordingly.

Additionally or alternatively, processing facility 104 may process the acoustic content contained in the first and second analysis channels by processing the acoustic content contained in the first and second analysis channels in accordance with a noise reduction heuristic. In other words, processing facility 104 may apply noise reduction to the acoustic content contained in the first and second analysis channels. Processing facility 104 may then generate a mixed signal by summing or otherwise combining the noise-reduced acoustic content contained in the first and second analysis channels.

Any suitable noise reduction heuristic may be used by processing facility 104 to reduce the amount of noise contained in the first and second analysis channels. For example, various noise reduction heuristics that may be employed by the systems and methods described herein are described in co-pending U.S. patent application Ser. No. 12/879,603, entitled "Methods and Systems for Reducing an Effect of Ambient Noise Within an Auditory Prosthesis System," filed Sep. 10, 2010, and incorporated herein by reference in its entirety.

Additionally or alternatively, processing facility 104 may process the acoustic content contained in the first and second analysis channels by processing the acoustic content contained in the first and second analysis channels in accordance with a binaural processing heuristic. As used herein, a "binaural processing heuristic" may include, but is not limited to, a head-related transfer function ("HRTF") processing heuristic, a beam-forming processing heuristic, and/or any other processing heuristic that is related to binaural hearing. Processing facility 104 may then generate a mixed signal by summing or otherwise combining the binaural-processed acoustic content contained in the first and second analysis channels.

Processing facility 104 may be further configured to direct one or more cochlear implants to apply electrical stimulation representative of the mixed acoustic content associated with each pair of corresponding analysis channels to various stimulation sites within one or both ears of the patient by way of stimulation channels that correspond to the pairs of corresponding analysis channels. As used herein, a "stimulation channel" may include one or more electrodes implanted within the patient.

For example, as mentioned above, processing facility 104 may generate a mixed signal by processing and mixing acoustic content contained in corresponding first and second analysis channels. In the case of a unilaterally implanted patient having a single cochlear implant associated with the first ear, processing facility 104 may direct the cochlear implant to apply electrical stimulation representative of the mixed signal to the first ear by way of a stimulation channel that corresponds to the first analysis channel. In the case of a bilaterally implanted patient having a first cochlear implant associated with the first ear and a second cochlear implant associated with the second ear, processing facility 104 may direct the first cochlear implant to apply electrical stimulation representative of the mixed signal (which, as will be described below, may be first adjusted to account for an interaural level difference between the first and second audio signals) to the first ear by way of a stimulation channel that corresponds to the first analysis channel and the second cochlear implant to apply electrical stimulation representative of the mixed signal (which, as will be described below, may also be adjusted to account for an interaural level difference between the first and second audio signals) to the second ear by way of a stimulation channel that corresponds to the second analysis channel.

Storage facility 106 may be configured to maintain acoustic content data 108 generated and/or used by spectral analysis facility 102 and/or processing facility 104 and/or processing data 110 generated and/or used by processing facility 104. It will be recognized that storage facility 106 may maintain additional or alternative data as may serve a particular implementation.

Figure 3:
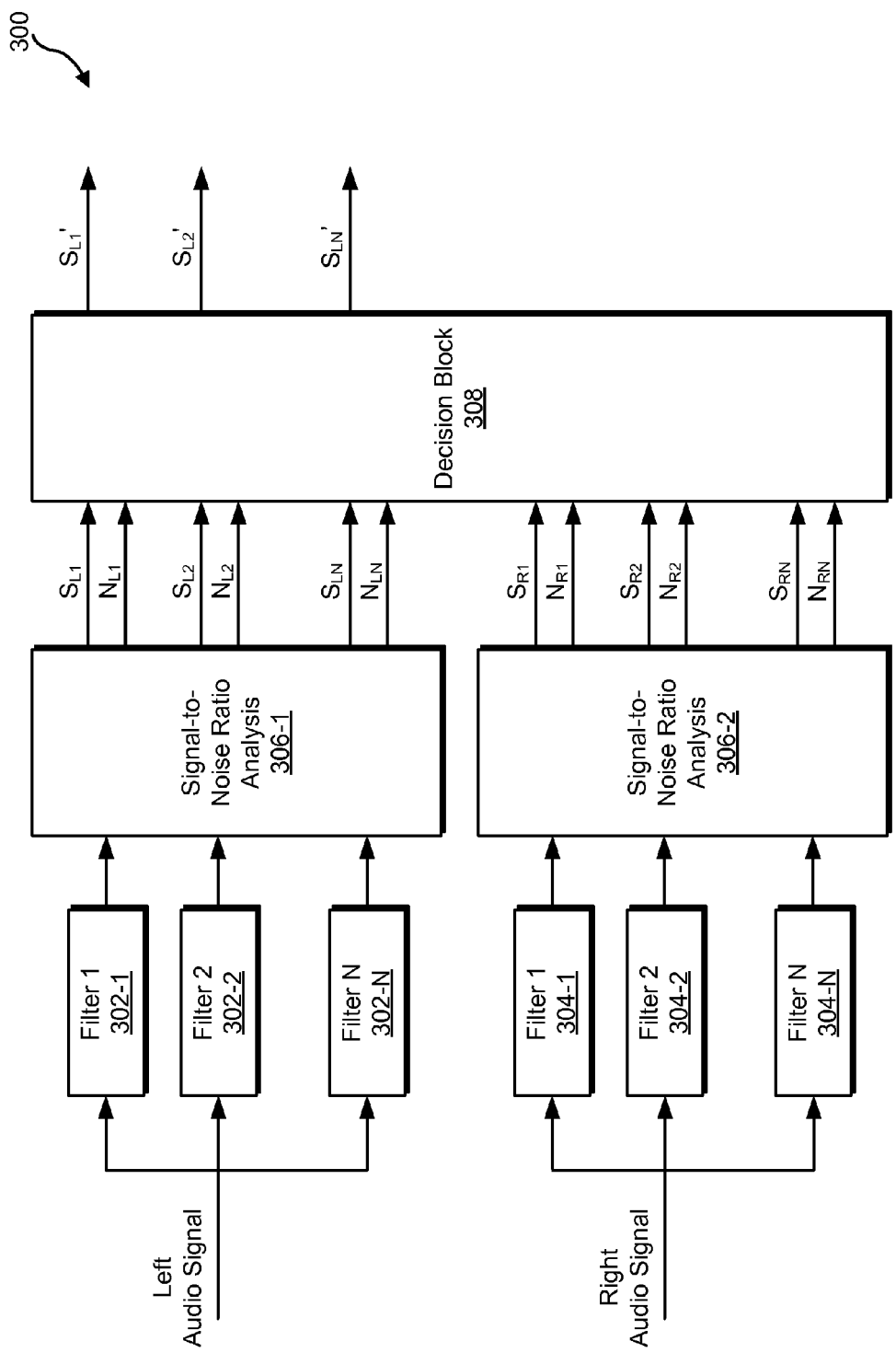
FIG. 3 illustrates an exemplary implementation of the system of FIG. 1 according to principles described herein.

FIG. 3 illustrates an exemplary implementation 300 of system 100 that may be used to facilitate binaural hearing by a unilateral cochlear implant patient. In the example of FIG. 3, the left ear of the patient has been fitted with a cochlear implant. It will be recognized that implementation 300 is merely illustrative of the many possible implementations of system 100 that may be realized for a unilateral cochlear implant patient. For example, other implementations that process audio signals presented to a unilateral cochlear implant patient in other ways may be realized in accordance with the systems and methods described herein.

As shown in FIG. 3, a left audio signal (i.e., an audio signal detected by a microphone positioned proximal to the left ear canal of the patient) may be divided into N analysis channels by filters 302-1 through 302-N (collectively "filters 302"). Similarly, a right audio signal (i.e., an audio signal detected by a microphone positioned proximal to the right ear canal of the patient) may be divided into N analysis channels by filters 304-1 through 304-N (collectively "filters 304"). As described previously, the left and right analysis channels include corresponding pairs of analysis channels.

Figure 5:
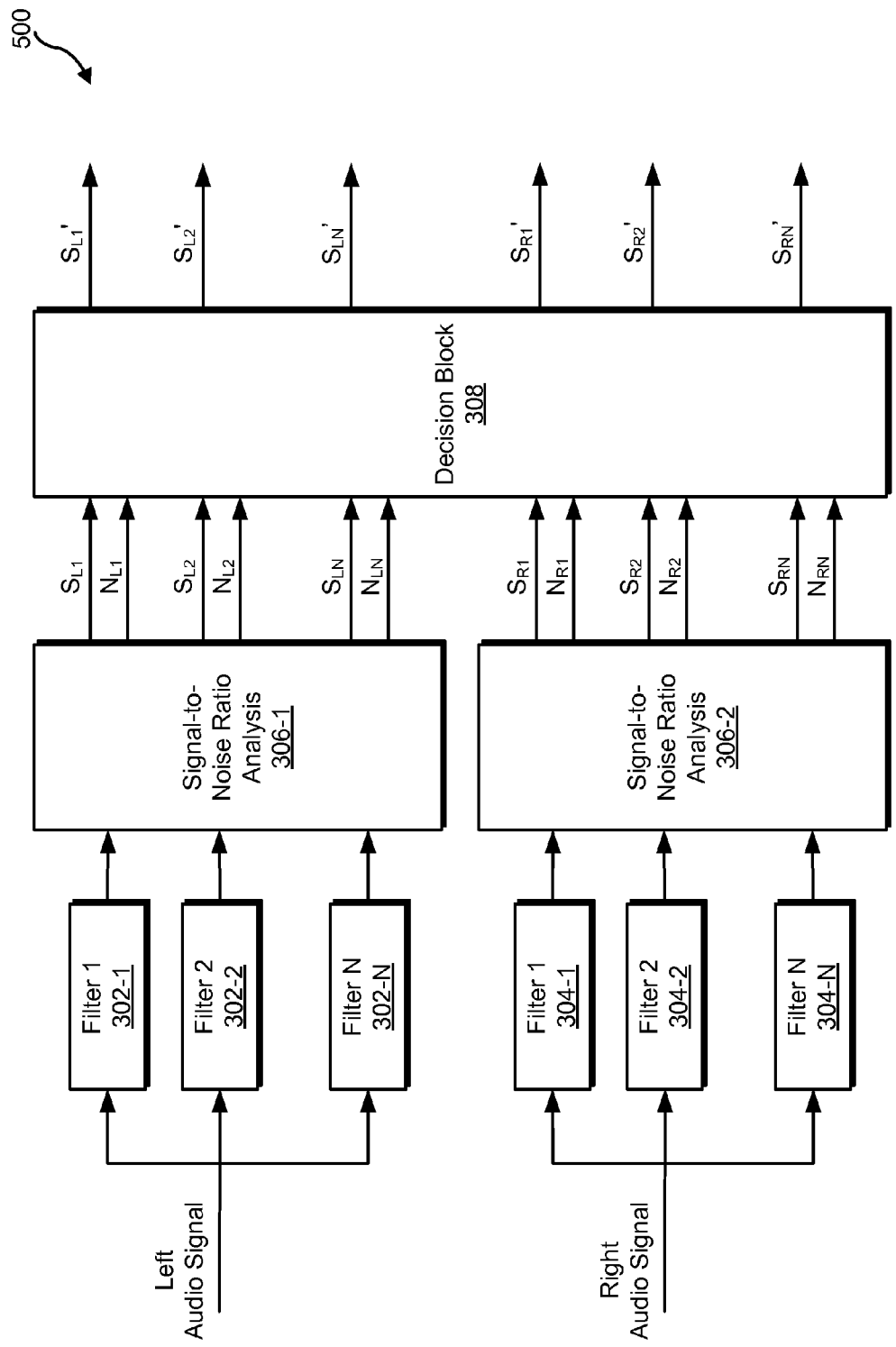
FIG. 5 illustrates another exemplary implementation of the system of FIG. 1 according to principles described herein.

Signal-to-noise ratio analysis blocks 306-1 and 306-2 (collectively "signal-to-noise ratio analysis blocks 306") may be configured to perform one or more signal-to-noise ratio analysis functions with respect to the acoustic content contained in each of the analysis channels generated by filters 302 and 304. For example, signal-to-noise ratio analysis blocks 306 may separate the audio content contained in each analysis channel into a signal component (e.g., a speech component, a music component, and/or other type of audio component including information of interest to the patient) and a noise component. The noise component may be identified and separated from the signal component using any suitable algorithm or process as may serve a particular application. As shown in FIG. 5, the signal components contained in the left analysis channels are labeled $S_{L1}$ through $S_{LN}$ and the noise components contained in the left analysis channels are labeled $N_{L1}$ through $N_{LN}$. Likewise, the signal components contained in the right analysis channels are labeled $S_{R1}$ through $S_{RN}$ and the noise components contained in the right analysis channels are labeled $N_{R1}$ through $N_{RN}$.

As shown, the signal and noise components for each analysis channel may be input into a decision block 308. Decision block 308 may be configured to process the signal and noise components and generate mixed signals $S_{L1}'$ through $S_{LN}'$ associated with each pair of corresponding analysis channels. Electrical stimulation representative of the mixed signals may then be applied to the left ear of the patient by way of stimulation channels that correspond to the left analysis channels.

Figure 4:
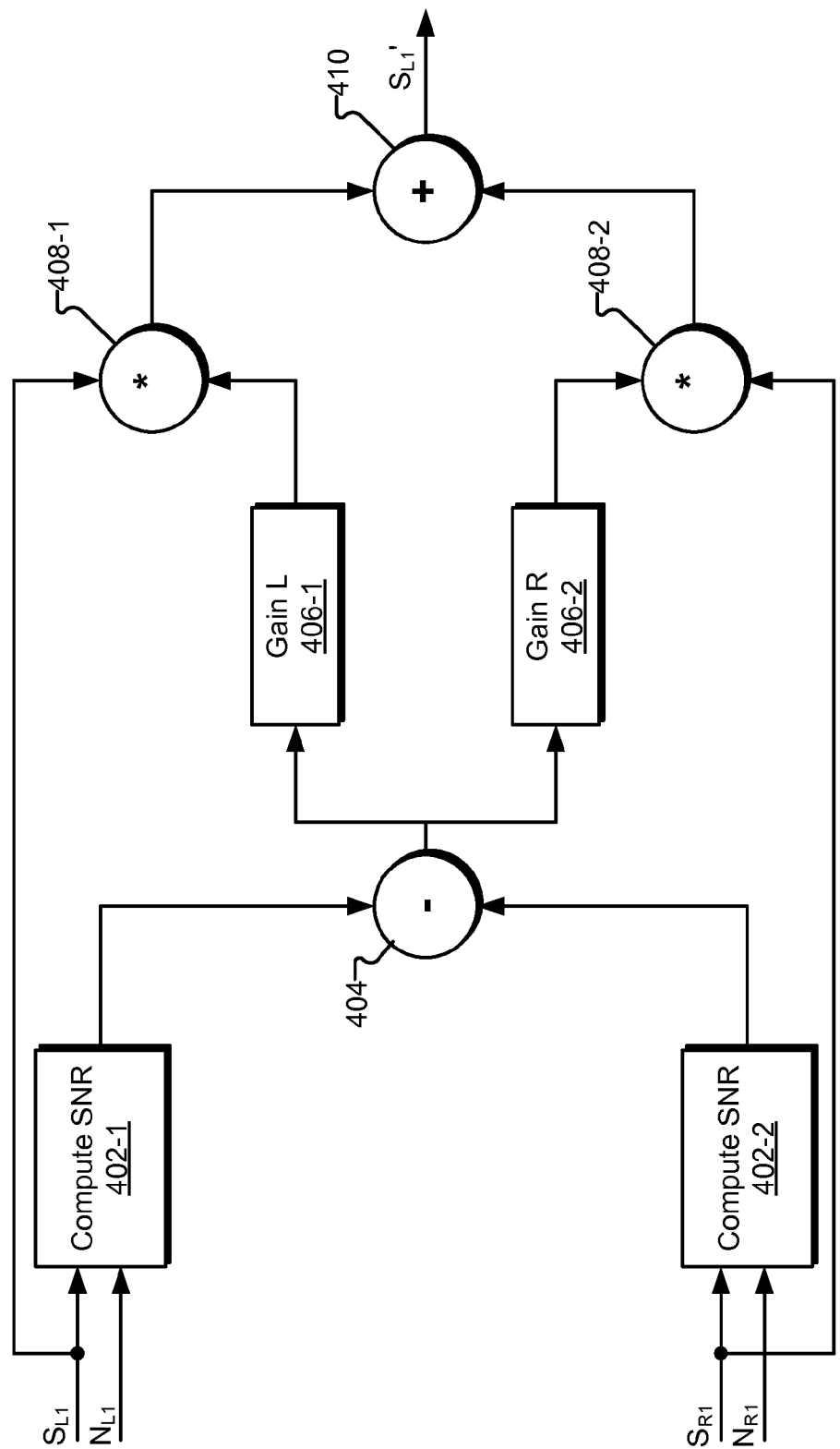
FIG. 4 illustrates exemplary functions that may be performed by a decision block illustrated in FIG. 3 with respect to a particular pair of corresponding analysis channels according to principles described herein.

FIG. 4 illustrates exemplary functions that may be performed by decision block 308 with respect to a particular pair of corresponding analysis channels (i.e., the first analysis channel included in each set of analysis channels). As shown, the signal-to-noise ratio of the acoustic content contained in each analysis channel may be computed at stages 402-1 and 402-2. The signal-to-noise ratios may be computed any suitable manner as may serve a particular implementation.

The signal-to-noise ratios of the acoustic content contained in each analysis channel may then be compared by subtracting the acoustic content contained in the right analysis channel from the acoustic content contained in the left analysis channel (subtraction block 404). The signal-to-noise ratios of the acoustic content contained in each analysis channel may be otherwise compared in any other suitable manner.

A gain (i.e., "gain L" and "gain R") may then be computed for the left and right analysis channels, respectively, at stages 406-1 and 406-2. As shown, the gains may be based on the difference between the signal-to-noise ratios of the acoustic content contained in each analysis channel. For example, if the difference in signal-to-noise ratios of the acoustic content is relatively high, a relatively higher gain may be computed for the acoustic content contained in the left analysis channel than for the acoustic content contained in the right analysis channel. In this manner, the acoustic content contained in the left channel is weighted relatively higher than the acoustic content contained in the right channel, which may result in the patient perceiving the acoustic content as originating from a source that is closer to the left ear than to the right ear.

The gains may then be applied to the acoustic content contained in each analysis channel. In some examples, as shown in FIG. 4, the gains are applied to the signal component of the acoustic content contained in each analysis channel. To illustrate, FIG. 4 shows that gain L is applied to signal component $S_{L1}$ using multiplication block 408-1 and that gain R is applied to signal component $S_{R1}$ using multiplication block 408-2.

The gain-adjusted acoustic content contained in the left and right analysis channels may then be mixed using summation block 410 and/or in any other manner as may serve a particular implementation. As shown, the mixed signal is labeled $S_{L1}'$. System 100 may then direct a cochlear implant associated with the left ear to apply electrical stimulation representative of mixed signal $S_{L1}'$ to the left ear by way of a stimulation channel that corresponds to the left analysis channel. In this manner, a sensation of binaural hearing may be created for the patient even though the patient is only implanted with a single cochlear implant.

FIG. 5 illustrates an exemplary implementation 500 of system 100 that may be used to facilitate and/or enhance binaural hearing by a bilateral cochlear implant patient. In the example of FIG. 5, both ears of the patient have been fitted with cochlear implants. It will be recognized that implementation 500 is merely illustrative of the many possible implementations of system 100 that may be realized for a bilateral cochlear implant patient. For example, other implementations that process audio signals presented to a bilateral cochlear implant patient in other ways may be realized in accordance with the systems and methods described herein.

Implementation 500 is similar to implementation 300 shown in FIG. 3 in that it includes filters 302, filters 304, signal-to-noise ratio analysis blocks 306, and decision block 308. However, as shown in FIG. 5, decision block 308 may be further configured to generate mixed signals $S_{R1}'$ through $S_{RN}'$ associated with each pair of corresponding analysis channels. Electrical stimulation representative of mixed signals $S_{R1}'$ through $S_{RN}'$ may then be applied to the right ear of the patient by way of stimulation channels that correspond to the right analysis channels.

Figure 6:
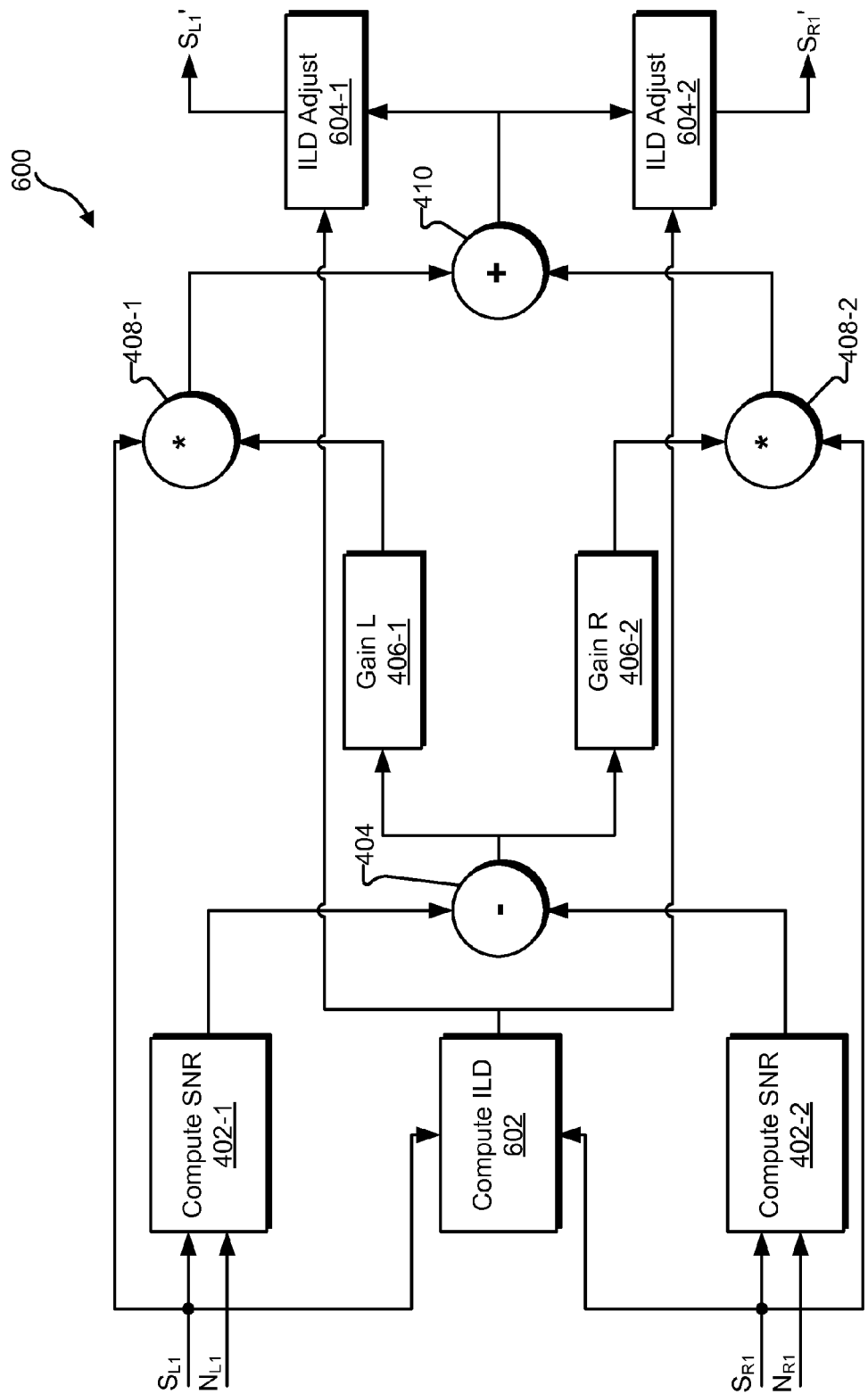
FIG. 6 illustrates exemplary functions that may be performed by a decision block shown in FIG. 5 with respect to a particular pair of corresponding analysis channels according to principles described herein.

FIG. 6 illustrates exemplary functions that may be performed by decision block 308 with respect to a particular pair of corresponding analysis channels (i.e., the first analysis channel included in each set of analysis channels) for a bilateral cochlear implant patient. Many of the functions shown in FIG. 6 are similar to those shown in FIG. 4. However, additional stages associated with accounting for an interaural level difference between the left and right audio signals are included in FIG. 6. As used herein, an "interaural level difference" refers to a sound level difference between the left and right audio signals as originally presented to the patient. This difference may be computed in stage 602 based on the signal components $S_{L1}$ and $S_{R1}$, for example. The output of the summation block 410 (i.e., the mixing stage) may be adjusted in accordance with the computed interaural level difference in stages 604-1 and 604-2 in order to facilitate perception of the relatively different sound levels. For example, if the sound level of the left audio signal is significantly higher than the sound level of the right audio signal, the output of the mixing stage for the right auditory channel may be attenuated, thereby resulting mixed signal $S_{R1}'$.

Figure 7:
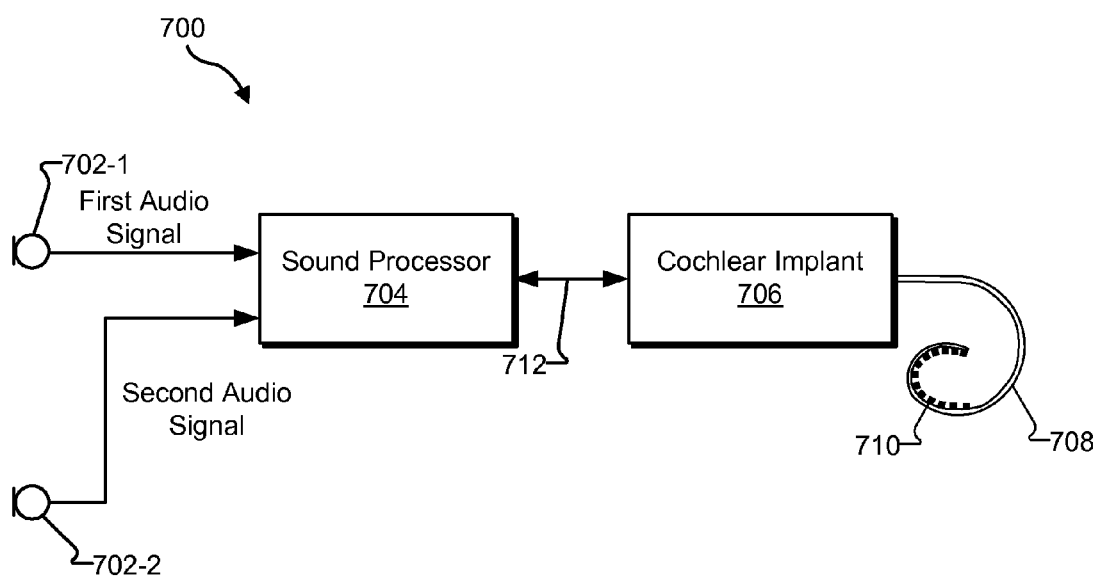
FIG. 7 illustrates an exemplary unilateral cochlear implant system that may be used in connection with the systems and methods described herein.

FIG. 7 illustrates an exemplary unilateral cochlear implant system 700 that may be used in connection with the systems and methods described herein. As shown, unilateral cochlear implant system 700 may include a first microphone 702-1, a second microphone 702-2, a sound processor 704, a cochlear implant 706, and an electrode lead 708 having a plurality of electrodes 710 disposed thereon.

First and second microphones 702-1 and 702-2 (collectively "microphones 702") may be configured to concurrently detect first and second audio signals presented to the left and right ears of the patient, respectively. For example, first microphone 702-1 may be positioned proximal to the left ear canal of the patient and second microphone 702-2 may be positioned proximal to the right ear canal of the patient. Various microphone arrangements that may be used to detect the first and second audio signals will be described below.

Sound processor 704 may include any suitable device configured to process the first and second audio signals detected by microphones 702. presented to a cochlear implant patient and/or control an operation of cochlear implant 706. In some examples, sound processor 704 is implemented by an externally worn unit (e.g., a behind-the-ear device, a body worn device, etc.). Alternatively, sound processor 704 may be configured to be at least partially implanted within the patient. One or more facilities included in system 100 may be implemented by sound processor 704.

Sound processor 704 may be communicatively coupled to both microphones 702-1 and 702-2 in any suitable manner as may serve a particular implementation. For example, sound processor 704 may be communicatively coupled to microphones 702-1 and 702-2 using a wired and/or wireless connection. Exemplary configurations in which a sound processor is communicatively coupled to microphones 702 will be described below.

Cochlear implant 706 may include any suitable auditory prosthesis configured to be at least partially implanted within a patient as may serve a particular implementation. For example, cochlear implant 706 may include an implantable cochlear stimulator, a brainstem implant and/or any other type of auditory prosthesis. Sound processor 704 and cochlear implant 706 may communicate by way of communication channel 712, which may be wired or wireless as may serve a particular implementation.

Electrode lead 708 may be implanted within the patient such that electrodes 710 are in communication with stimulation sites within the cochlea and/or anywhere else along the auditory pathway of the patient. In this configuration, sound processor 704 may direct cochlear implant 706 to apply electrical stimulation representative of an audio signal to one or more stimulation sites within the patient by way of one or more stimulation channels formed by electrodes 710.

Figure 8:
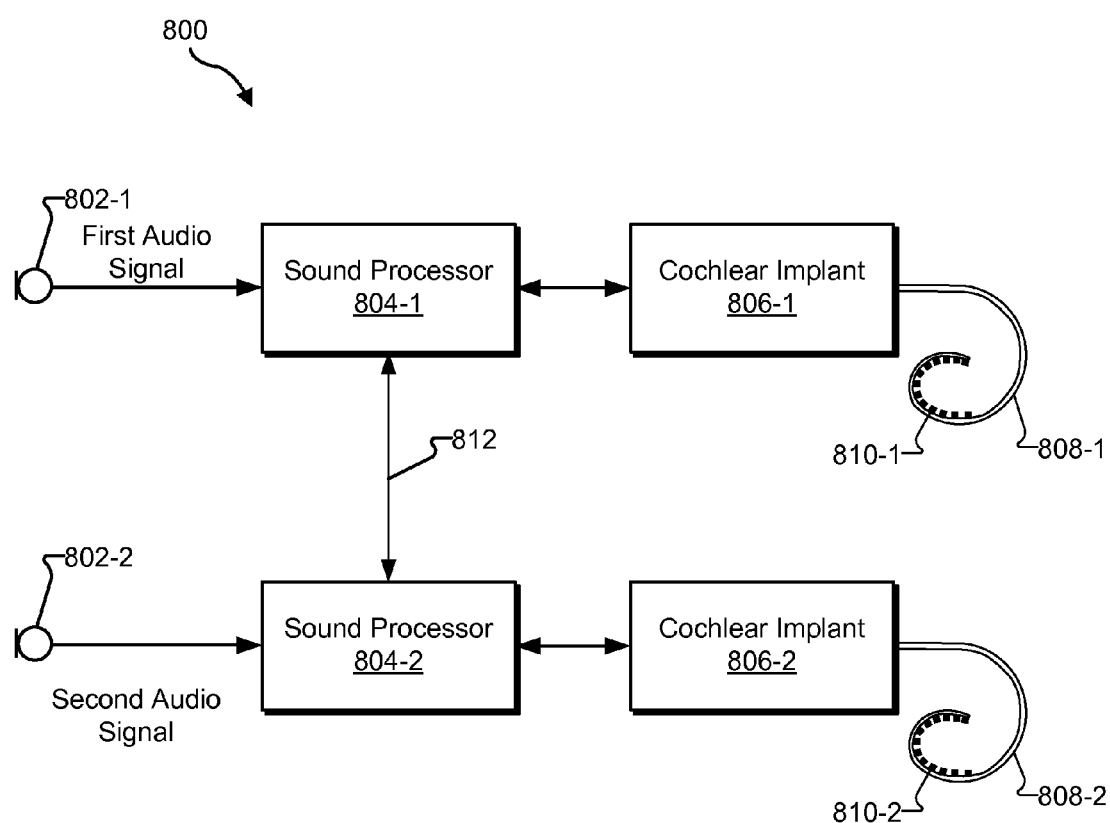
FIG. 8 illustrates an exemplary bilateral cochlear implant system that may be used in connection with the systems and methods described herein.

FIG. 8 illustrates an exemplary bilateral cochlear implant system 800 that may be used in connection with the systems and methods described herein. As shown, bilateral cochlear implant system 800 may include first and second microphones 802-1 and 802-2 (collectively "microphones 802"), first and second sound processors 804-1 and 804-2 ("collectively "sound processors 804"), cochlear implants 806-1 and 806-2 ("collectively "cochlear implants 806"), and electrode leads 808-1 and 808-2, each having electrodes 810 (e.g., electrodes 810-1 and 810-2) disposed thereon. Microphone 802-1, sound processor 804-1, cochlear implant 806-1, electrode lead 808-1 and electrodes 810-1 are associated with a first ear (e.g., the left ear) of the patient and microphone 802-2, sound processor 804-2, cochlear implant 806-2, electrode lead 808-2 and electrodes 810-2 are associated with a second ear (e.g., the right ear) of the patient.

As shown, sound processors 804-1 and 804-2 may be configured to communicate by way of communication channel 812, which may be wired or wireless as may serve a particular implementation. Communication channel 812 may facilitate transmission of data representative of the first and second audio signals between sound processors 804. In this manner, each facility included in system 100 may be implemented by sound processor 804-1, sound processor 804-2, and/or a combination thereof. For example, sound processor 804-1 may be configured to process a first audio signal detected by microphone 802-1 and transmit data representative of the processed first audio signal to sound processor 804-2, which may compare and/or mix the received data with data representative of a second audio signal detected by microphone 802-2. Likewise, sound processor 804-2 may be configured to process the second audio signal detected by microphone 802-2 and transmit data representative of the processed second audio signal to sound processor 804-1, which may compare and/or mix the received data with data representative of the first audio signal detected by microphone 802-1.

Various physical arrangements that may be used to detect, process, and/or mix audio signals presented to both ears of a unilateral cochlear implant patient will now be described in connection with FIGS. 9-13. It will be recognized that the physical arrangements described in connection with FIGS. 9-13 are merely illustrative of the many possible physical arrangements that may be realized in connection with the systems and methods described herein.

Figure 9:
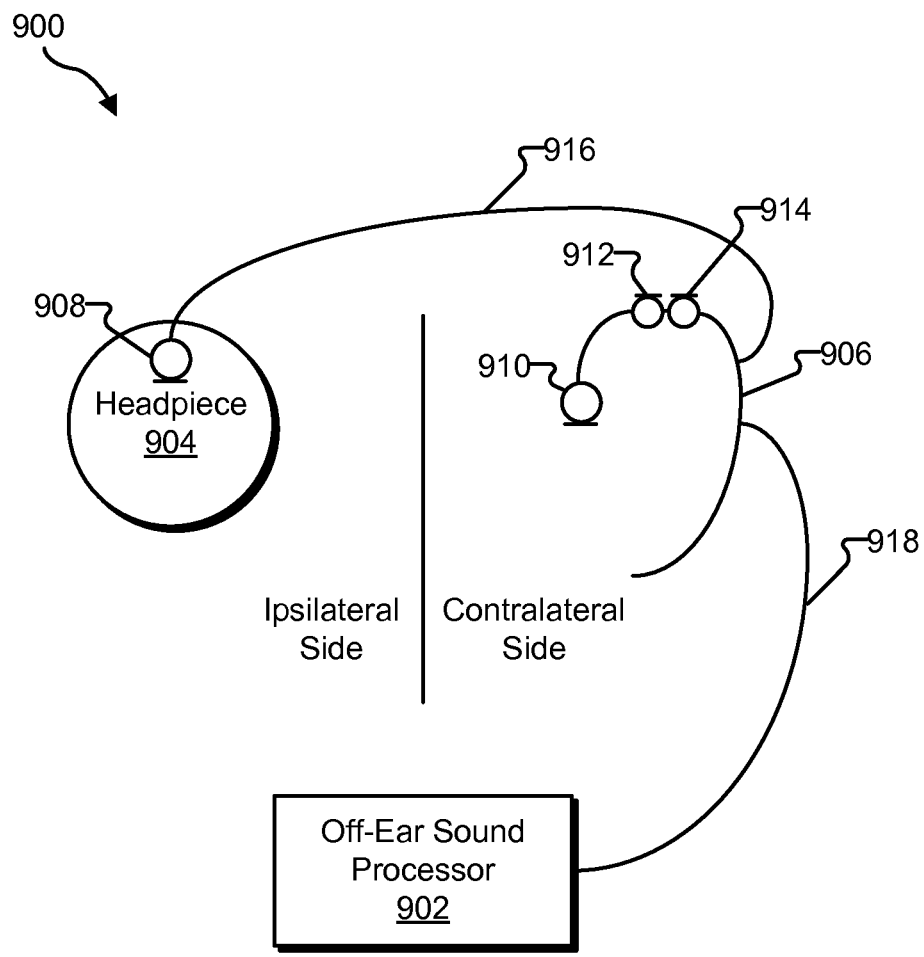
FIGS. 9-13 show exemplary physical arrangements that may be used to detect, process, and/or mix audio signals presented to both ears of a unilateral cochlear implant patient according to principles described herein.

FIG. 9 shows an exemplary arrangement 900 in which a unilateral cochlear implant patient is fitted with an off-ear sound processor 902 (i.e., a sound processor configured to be worn off the ear of the patient) configured to control a cochlear implant associated with a particular ear of the patient (i.e., the left ear of the patient). As shown, arrangement 900 may further include a headpiece 904 configured to be attached to the patient's head such that it is in communication with the cochlear implant and an earhook 906 configured to be worn on the opposite ear (e.g., the right ear) of the patient. Hence, as shown, headpiece 904 is located on an "ipsilateral side" of the patient (i.e., on the same side of the patient as the cochlear implant) and earhook 906 is located on a "contralateral" side of the patient (i.e., on an opposite side of the patient as the cochlear implant).

As shown, headpiece 904 may include a microphone 908 disposed therein, which may be configured to detect audio signals presented to the ipsilateral side of the patient. Likewise, earhook 906 may include a microphone 910 (e.g., a T-MIC) configured to be positioned proximal to the contralateral ear canal of the patient and/or one or more ear-level microphones (e.g., microphones 912 and 914). Inclusion of multiple microphones (e.g., microphones 910, 912, and 914) may facilitate beam-forming. However, it will be recognized that earhook 906 may alternatively include only a single microphone (e.g., microphone 910).

As shown, earhook 906 may be communicatively coupled to microphone 908 included in headpiece 904 by way of cable 916 and to off-ear sound processor 902 by way of cable 918. Cables 916 and 918 may each include a coax cable, a multi-conductor cable, a digital bus cable, and/or one or more wires. In this configuration, audio signals detected by microphone 908 may be routed to off-ear sound processor 902 by way of cables 916 and 918, audio signals detected by microphones 910, 912, and/or 914 may be routed to off-ear sound processor 902 by way of cable 918, and off-ear sound processor 902 may transmit control parameters to the cochlear implant by way of cables 918 and 916. In some alternative embodiments, microphone 908 may be connected directly to off-ear sound processor 902.

In some examples, earhook 906 may be configured to perform at least one or more processing operations on audio signals detected by any of microphones 908, 910, 912, and/or 914. For example, earhook 906 may include one or more components configured to multiplex the audio signals, mix the audio signals, digitize the audio signals, and/or transmit the audio signals to off-ear sound processor 902 for further processing (e.g., in a time-division-multiplexed manner). Hence, system 100 may be implemented by any combination of earhook 906 and off-ear sound processor 902 as may serve a particular implementation.

Figure 10:
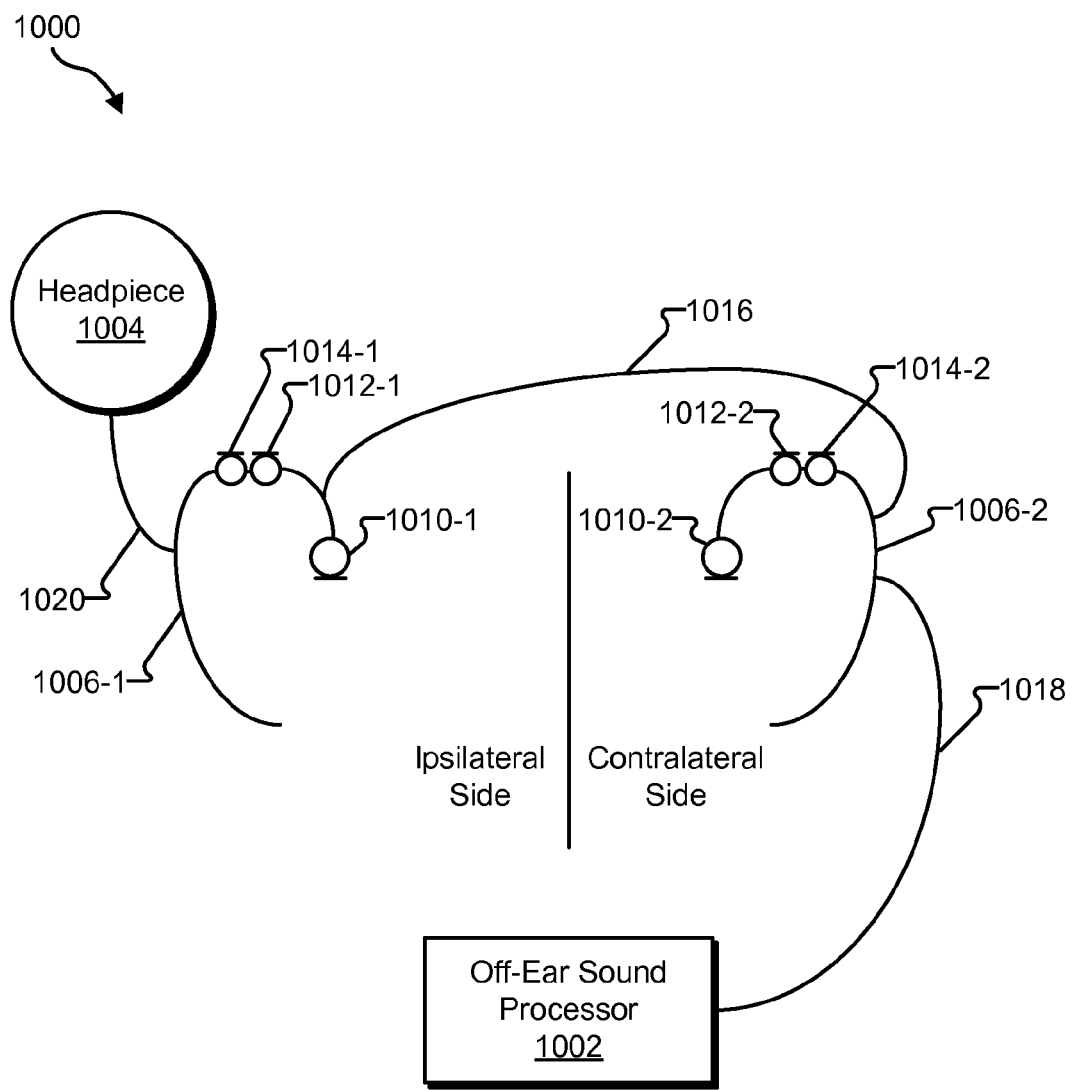

FIG. 10 shows another exemplary arrangement 1000 in which a unilateral cochlear implant patient is fitted with an off-ear sound processor 1002. As shown, arrangement 1000 may further include a headpiece 1004 configured to be attached to the patient's head such that it is in communication with an implanted cochlear implant, an earhook 1006-1 configured to be worn on the ipsilateral ear, and an earhook 1006-2 configured to be worn on the contralateral ear. Off-ear sound processor 1002, headpiece 1004, and earhooks 1006-1 and 1006-2 may be similar to those described in connection with FIG. 9. Hence, system 100 may be implemented by any combination of earhooks 1006-1 and 1006-2 and off-ear sound processor 1002 as may serve a particular implementation.

As shown, earhook 1006-1 may include microphones 1010-1, 1012-1, and 1014-1 configured to detect audio signals presented to the ipsilateral side of the patient and earhook 1006-2 may include microphones 1010-2, 1012-2, and 1014-2 configured to detect audio signals presented to the contralateral side of the patient. Audio signals detected by microphones 1010-1, 1012-1, and/or 1014-1 may be routed to off-ear sound processor 1002 by way of cable 1016, which connects earhook 1006-1 to earhook 1006-2, and cable 1018, which connects earhook 1006-2 to off-ear sound processor 1002.

Headpiece 1006-1 may be further connected to headpiece 1004 by way of cable 1018. In this arrangement, off-ear sound processor 1002 may transmit control parameters to the cochlear implant by way of cables 1018, 1016, and 1020.

Figure 11:
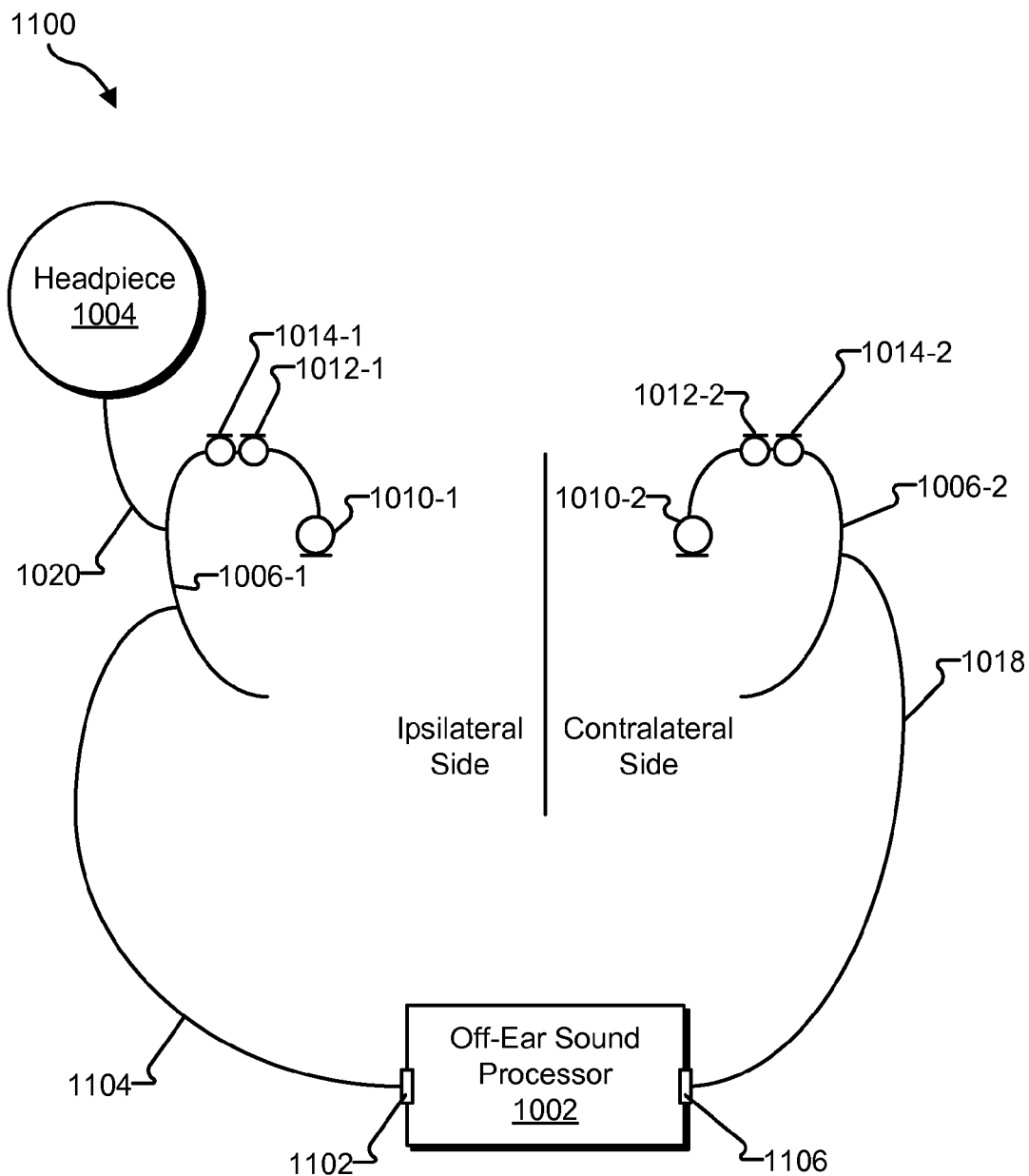

FIG. 11 shows another exemplary arrangement 1100 in which a unilateral cochlear implant patient is fitted with off-ear sound processor 1002. Arrangement 1100 is similar to arrangement 1000, except that both earhooks 1006-1 and 1006-2 are connected directly to off-ear sound processor 1002. For example, earhook 1006-1 may be connected to a headpiece jack 1102 of off-ear sound processor 1002 (i.e., a jack normally used to connect directly to headpiece 1004) by way of cable 1104 and earhook 1006-2 may be connected to an auxiliary input port 1106 of off-ear sound processor 1002 by way of cable 1018.

Figure 12:
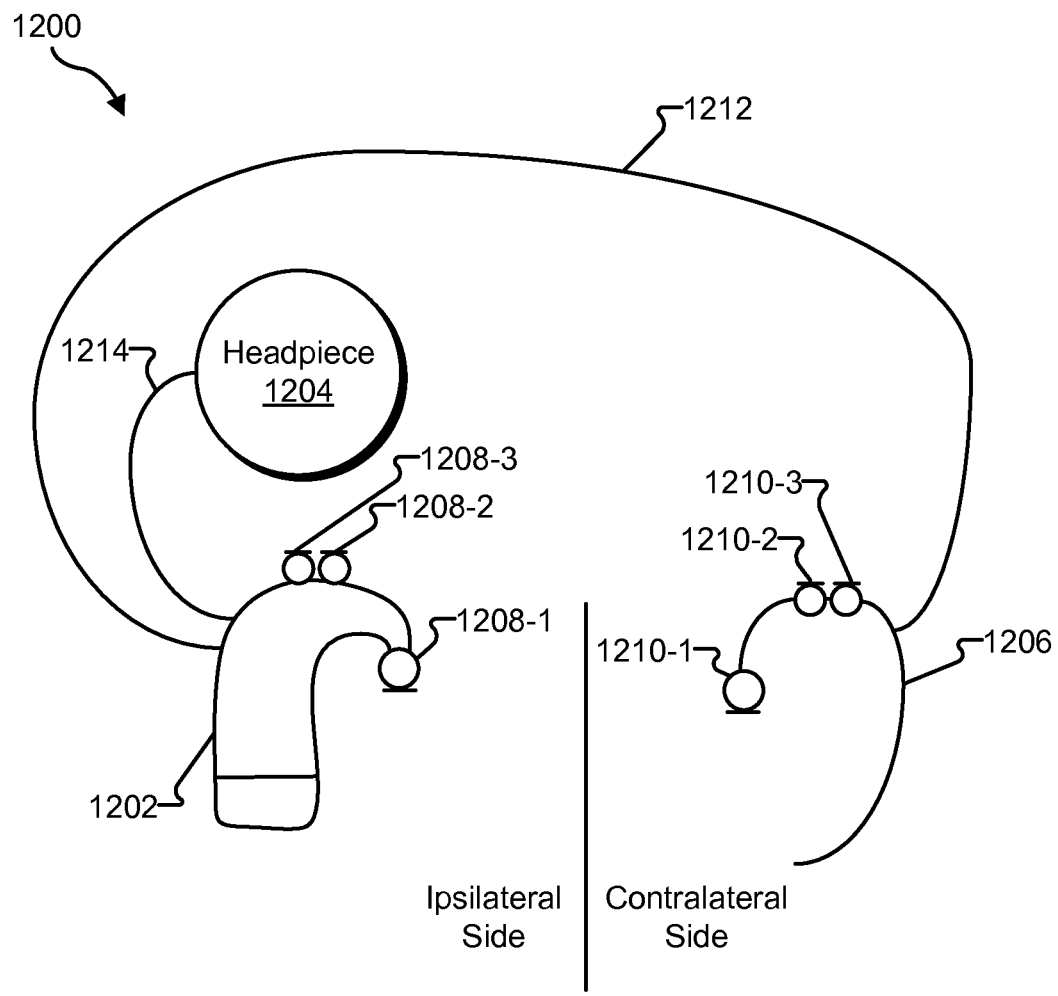

FIG. 12 shows an exemplary arrangement 1200 in which a unilateral cochlear implant patient is fitted with a behind-the-ear ("BTE") sound processor 1202. As shown, arrangement 1200 may further include a headpiece 1204 configured to be attached to the patient's head such that it is in communication with an implanted cochlear implant and an earhook 1206 configured to be worn on the contralateral ear. Headpiece 1204 and earhook 1206 may be similar to those described in connection with FIG. 9. System 100 may be implemented by any combination of BTE sound processor 1202 and earhook 1206 as may serve a particular implementation.

As shown, BTE processor 1202 may include microphones 1208-1 through 1208-3 configured to detect audio signals presented to the ipsilateral side of the patient and earhook 1206 may include microphones 1210-1 through 1210-3 configured to detect audio signals presented to the contralateral side of the patient. Audio signals detected by microphones 1210-1 through 1210-3 may be routed to BTE sound processor 1202 by way of cable 1212, which connects earhook 1206 to BTE sound processor 1202. BTE sound processor 1202 may process and mix the audio signals detected by any of the microphones shown in FIG. 12 and transmit control parameters to the cochlear implant by way of headpiece 1204 and cable 1214, which connects BTE sound processor 1202 to headpiece 1204.

Figure 13:
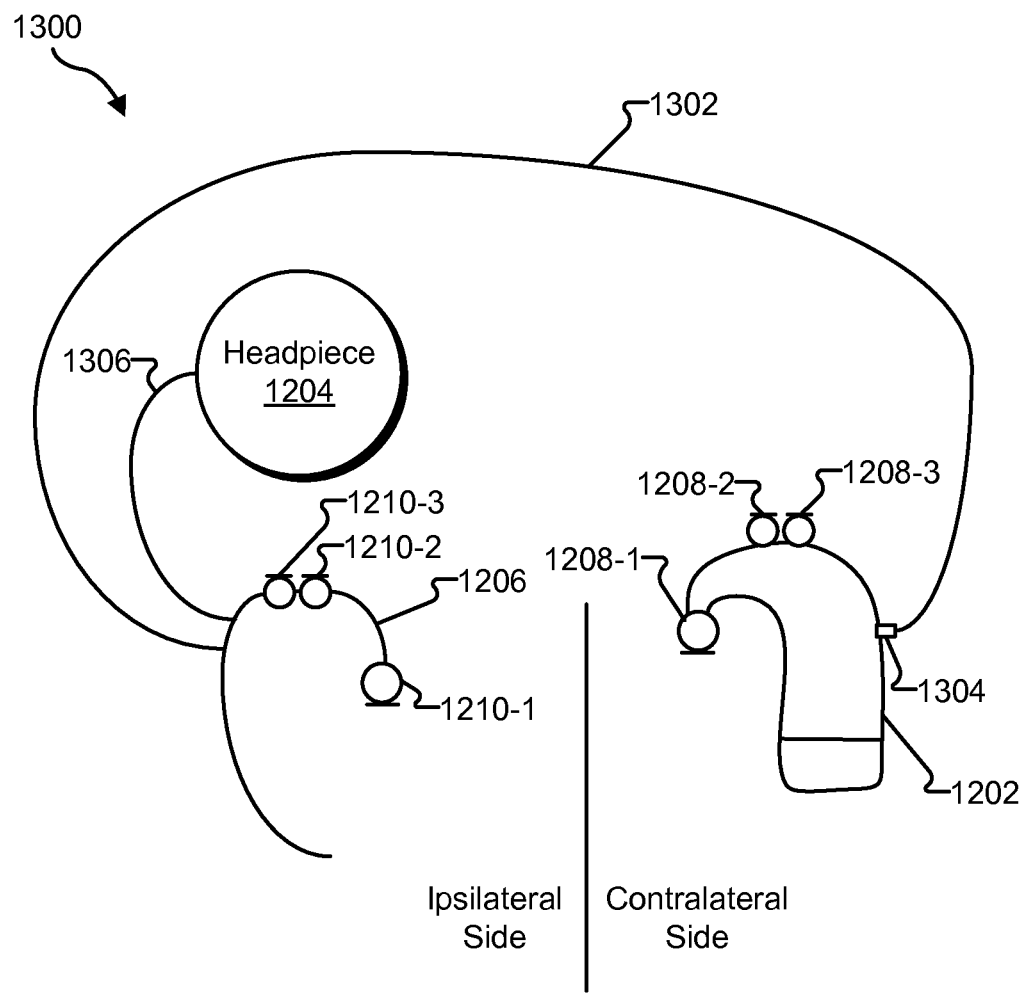

FIG. 13 shows another exemplary arrangement 1300 in which a unilateral cochlear implant patient is fitted with behind-the-ear ("BTE") sound processor 1202. Arrangement 1300 is similar to arrangement 1200, except that BTE sound processor 1306 is located on the contralateral side and earhook 1206 is located on the ipsilateral side. In this arrangement, earhook 1206 is connected to BTE sound processor 1202 by way of cable 1302, which may connect to BTE sound processor 1202 by way of a headpiece jack 1304 (i.e., a jack normally used to connect directly to headpiece 1204). Earhook 1206 is also connected to headpiece 1204 by way of cable 1306, which facilitates communication of BTE sound processor 1202 with the cochlear implant.

It will be recognized that although cables have been shown to communicatively couple the various components shown in FIGS. 9-13, any of the components may alternatively communicate wirelessly one with another.

Figure 14:
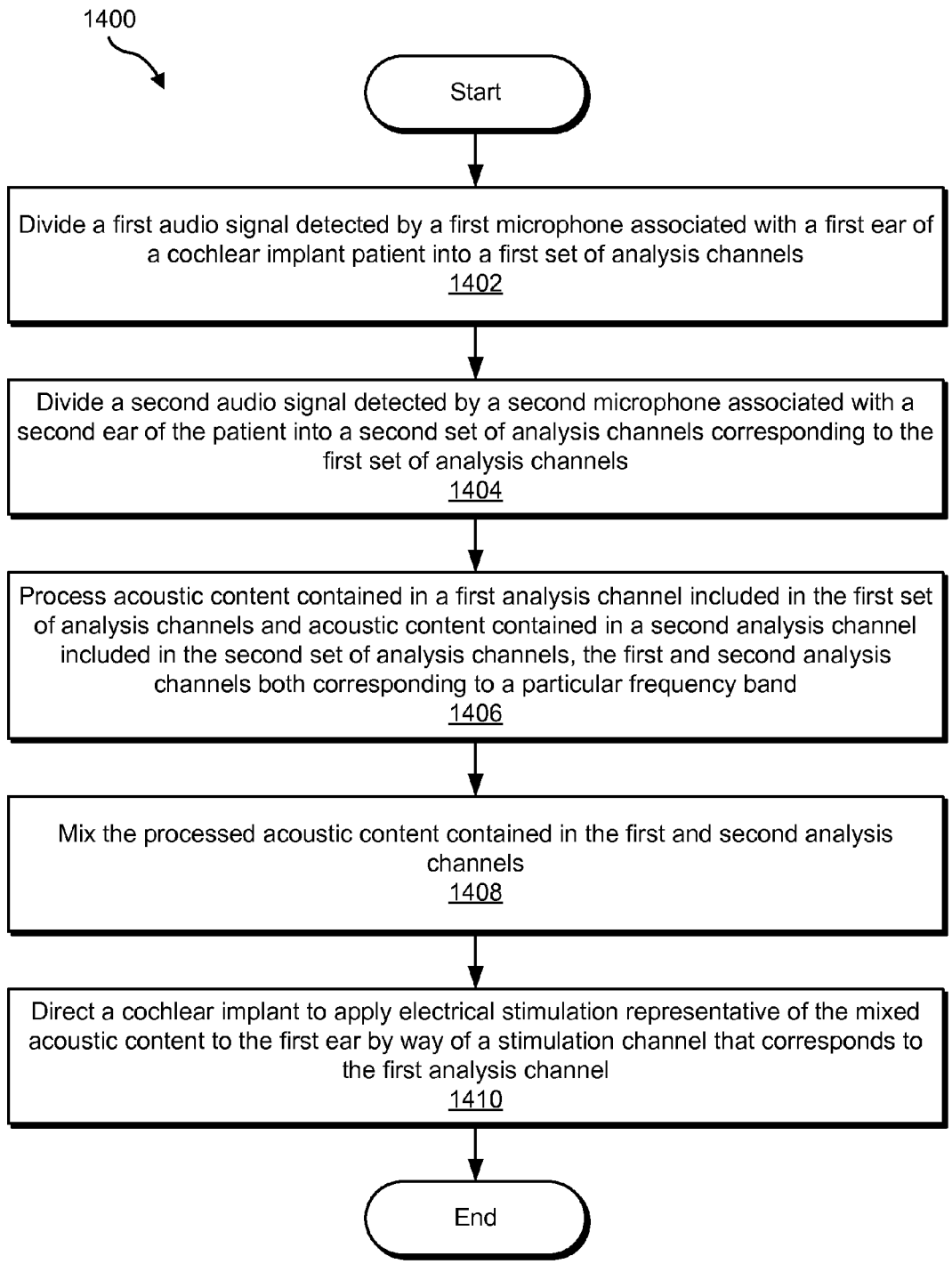
FIG. 14 illustrates an exemplary method of facilitating binaural hearing by a cochlear implant patient according to principles described herein.

FIG. 14 illustrates an exemplary method 1400 of facilitating binaural hearing by a cochlear implant patient. While FIG. 14 illustrates exemplary steps according to one embodiment, other embodiments may omit, add to, reorder, and/or modify any of the steps shown in FIG. 14. One or more of the steps shown in FIG. 14 may be performed by system 100 and/or any implementation thereof.

In step 1402, a sound processing system divides a first audio signal detected by a first microphone associated with a first ear of a cochlear implant patient into a first set of analysis channels. Step 1402 may be performed in any of the ways described herein.

In step 1404, the sound processing system divides a second audio signal detected by a second microphone associated with a second ear of the patient into a second set of analysis channels corresponding to the first set of analysis channels. Step 1404 may be performed in any of the ways described herein.

In step 1406, the sound processing system processes acoustic content contained in a first analysis channel included in the first set of analysis channels and acoustic content contained in a second analysis channel included in the second set of analysis channels. As mentioned, the first and second analysis channels both correspond to the same frequency band. Step 1406 may be performed in any of the ways described herein.

In step 1408, the sound processing system mixes the processed acoustic content contained in the first and second analysis channels. Step 1408 may be performed in any of the ways described herein.

In step 1410, the sound processing system directs a cochlear implant to apply electrical stimulation representative of the mixed acoustic content to the first ear by way of a stimulation channel that corresponds to the first analysis channel. Step 1410 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a spectral analysis facility configured to
      divide a first audio signal detected by a first microphone associated with a first ear of a cochlear implant patient into a first set of analysis channels, and
      divide a second audio signal detected by a second microphone associated with a second ear of the patient into a second set of analysis channels corresponding to the first set of analysis channels; and
   a processing facility communicatively coupled to the spectral analysis facility and configured to
      process, in accordance with a binaural processing heuristic, acoustic content contained in a first analysis channel included in the first set of analysis channels and acoustic content contained in a second analysis channel included in the second set of analysis channels, the first and second analysis channels both corresponding to a particular frequency band,
      mix the processed acoustic content contained in the first and second analysis channels, and
      direct a cochlear implant to apply electrical stimulation representative of the mixed acoustic content to the first ear by way of a stimulation channel that corresponds to the first analysis channel.

2. The system of claim 1, wherein the processing facility is further configured to process the acoustic content contained in the first analysis channel and the acoustic content contained in the second analysis channel by:
   comparing the acoustic content contained in the first analysis channel with the acoustic content contained in the second analysis channel;
   applying a gain to the acoustic content contained in the first analysis channel in accordance with the comparison; and
   applying a gain to the acoustic content contained in the second analysis channel in accordance with the comparison.

3. The system of claim 2, wherein the processing facility is configured to perform the comparing by comparing a signal-to-noise ratio of the acoustic content contained in the first analysis channel with a signal-to-noise ratio of the acoustic content contained in the second analysis channel.

4. A system comprising:
   a spectral analysis facility configured to
      divide a first audio signal detected by a first microphone associated with a first ear of a cochlear implant patient into a first set of analysis channels, and
      divide a second audio signal detected by a second microphone associated with a second ear of the patient into a second set of analysis channels corresponding to the first set of analysis channels; and a processing facility communicatively coupled to the spectral analysis facility and configured to process acoustic content contained in a first analysis channel included in the first set of analysis channels and acoustic content contained in a second analysis channel included in the second set of analysis channels, the first and second analysis channels both corresponding to a particular frequency band, mix the processed acoustic content contained in the first and second analysis channels, and direct a cochlear implant to apply electrical stimulation representative of the mixed acoustic content to the first ear by way of a stimulation channel that corresponds to the first analysis channel;

wherein the processing facility is configured to process the acoustic content contained in the first analysis channel and the acoustic content contained in the second analysis channel by:

comparing a signal-to-noise ratio of the acoustic content contained in the first analysis channel with a signal-to-noise ratio of the acoustic content contained in the second analysis channel;

determining a first gain and a second gain based on a difference between the signal-to-noise ratio of the acoustic content contained in the first analysis channel and the signal-to-noise ratio of the acoustic content contained in the second analysis channel;

applying the first gain to the acoustic content contained in the first analysis channel; and applying the second gain to the acoustic content contained in the second analysis channel.

5. The system of claim 3, wherein the processing facility is further configured to remove a noise component from the acoustic content contained in the first analysis channel and a noise component from the acoustic content contained in the second analysis channel before applying the gains to the acoustic content contained in the first analysis channel and to the acoustic content contained in the second analysis channel.

6. The system of claim 2, wherein the processing facility is configured to perform the comparing by comparing an energy level of the acoustic content contained in the first analysis channel with an energy level of the acoustic content contained in the second analysis channel.

7. The system of claim 2, wherein the processing facility is configured to perform the comparing by determining a level of correlation between the acoustic content contained in the first analysis channel and the acoustic content contained in the second analysis channel.

8. The system of claim 1, wherein the processing facility is further configured to process the acoustic content contained in the first analysis channel and the acoustic content contained in the second analysis channel by processing the acoustic content contained in the first analysis channel and the acoustic content contained in the second analysis channel in accordance with a noise reduction heuristic.

9. The system of claim 1, wherein the processing facility is further configured to:

adjust the mixed acoustic content to account for an interaural level difference between the first and second audio signals; and perform the directing by directing the cochlear implant to apply electrical stimulation representative of the adjusted mixed acoustic content to the first ear by way of the stimulation channel.

10. The system of claim 1, wherein the processing facility is further configured to:

adjust the mixed acoustic content to account for an interaural level difference between the first and second audio signals; and direct an additional cochlear implant to apply electrical stimulation representative of the adjusted mixed acoustic content to the second ear by way of a stimulation channel that corresponds to the analysis channel included in the second set of analysis channels.

11. A system comprising:

a spectral analysis facility configured to divide a first audio signal detected by a first microphone associated with a first ear of a cochlear implant patient into a first set of analysis channels, and divide a second audio signal detected by a second microphone associated with a second ear of the patient into a second set of analysis channels corresponding to the first set of analysis channels; and a processing facility communicatively coupled to the spectral analysis facility and configured to process acoustic content contained in a first analysis channel included in the first set of analysis channels and acoustic content contained in a second analysis channel included in the second set of analysis channels, the first and second analysis channels both corresponding to a particular frequency band, mix the processed acoustic content contained in the first and second analysis channels, and direct a cochlear implant to apply electrical stimulation representative of the mixed acoustic content to the first ear by way of a stimulation channel that corresponds to the first analysis channel;

wherein the processing facility is further configured to:

process acoustic content contained in a third analysis channel included in the first set of analysis channels and acoustic content contained in a fourth analysis channel included in the second set of analysis channels, the third and fourth analysis channels both corresponding to another particular frequency band;

mix the processed acoustic content contained in the third and fourth analysis channels; and direct the cochlear implant to apply electrical stimulation representative of the mixed acoustic content associated with the third and fourth analysis channels to the first ear by way of a stimulation channel that corresponds to the third analysis channel.

12. A method comprising:

dividing, by a sound processing system, a first audio signal detected by a first microphone associated with a first ear of a cochlear implant patient into a first set of analysis channels;

dividing, by the sound processing system, a second audio signal detected by a second microphone associated with a second ear of the patient into a second set of analysis channels corresponding to the first set of analysis channels;

processing, by the sound processing system in accordance with a binaural processing heuristic, acoustic content contained in a first analysis channel included in the first set of analysis channels and acoustic content contained in a second analysis channel included in the second set of analysis channels, the first and second analysis channels both corresponding to a particular frequency band;

mixing, by the sound processing system, the processed acoustic content contained in the first and second analysis channels; and directing, by the sound processing system, a cochlear implant to apply electrical stimulation representative of the mixed acoustic content to the first ear by way of a stimulation channel that corresponds to the first analysis channel.

13. The method of claim 12, wherein the processing comprises:

comparing the acoustic content contained in the first analysis channel with the acoustic content contained in the second analysis channel;

applying a gain to the acoustic content contained in the first analysis channel in accordance with the comparison; and applying a gain to the acoustic content contained in the second analysis channel in accordance with the comparison.

14. The method of claim 13, wherein the comparing comprises comparing a signal-to-noise ratio of the acoustic content contained in the first analysis channel with a signal-to-noise ratio of the acoustic content contained in the second analysis channel.

15. The method of claim 14, further comprising determining the gain that is applied to the acoustic content contained in the first analysis channel and the gain that is applied to the acoustic content contained in the second analysis channel based on a difference between the signal-to-noise ratio of the acoustic content contained in the first analysis channel and the signal-to-noise ratio of the acoustic content contained in the second analysis channel.

16. The method of claim 14, wherein the processing further comprises processing the acoustic content contained in the first analysis channel and the acoustic content contained in the second analysis channel in accordance with a noise reduction heuristic before the gains are applied to the acoustic content contained in the first analysis channel and to the acoustic content contained in the second analysis channel.

17. The method of claim 13, wherein the comparing comprises comparing an energy level of the acoustic content contained in the first analysis channel with an energy level of the acoustic content contained in the second analysis channel.

18. The method of claim 13, wherein the comparing comprises determining a level of correlation between the acoustic content contained in the first analysis channel and the acoustic content contained in the second analysis channel.

19. The method of claim 12, wherein the processing comprises processing the acoustic content contained in the first analysis channel and the acoustic content contained in the second analysis channel in accordance with a noise reduction heuristic.

20. The method of claim 12, further comprising:

adjusting, by the sound processing system, the mixed acoustic content to account for an interaural level difference between the first and second audio signals;

wherein the directing of the cochlear implant to apply electrical stimulation representative of the mixed acoustic content to the first ear by way of the stimulation channel comprises directing the cochlear implant to apply electrical stimulation representative of the adjusted mixed acoustic content to the first ear by way of the stimulation channel.

21. The method of claim 12, further comprising:

adjusting, by the sound processing system, the mixed acoustic content to account for an interaural level difference between the first and second audio signals; and directing, by the sound processing system, an additional cochlear implant to apply electrical stimulation representative of the adjusted mixed acoustic content to the second ear by way of a stimulation channel that corresponds to the analysis channel included in the second set of analysis channels.

22. The method of claim 12, further comprising:

processing, by the sound processing system, acoustic content contained in a third analysis channel included in the first set of analysis channels and acoustic content contained in a fourth analysis channel included in the second set of analysis channels, the third and fourth analysis channels both corresponding to another particular frequency band;

mixing, by the sound processing system, the processed acoustic content contained in the third and fourth analysis channels; and directing, by the sound processing system, the cochlear implant to apply electrical stimulation representative of the mixed acoustic content associated with the third and fourth analysis channels to the first ear by way of a stimulation channel that corresponds to the third analysis channel.

23. The system of claim 4, wherein the processing facility is further configured to remove a noise component from the acoustic content contained in the first analysis channel and a noise component from the acoustic content contained in the second analysis channel before applying the first gain to the acoustic content contained in the first analysis channel and the second gain to the acoustic content contained in the second analysis channel.

24. The system of claim 4, wherein the processing facility is further configured to:

adjust the mixed acoustic content to account for an interaural level difference between the first and second audio signals; and perform the directing by directing the cochlear implant to apply electrical stimulation representative of the adjusted mixed acoustic content to the first ear by way of the stimulation channel.

25. The system of claim 4, wherein the processing facility is further configured to:

adjust the mixed acoustic content to account for an interaural level difference between the first and second audio signals; and direct an additional cochlear implant to apply electrical stimulation representative of the adjusted mixed acoustic content to the second ear by way of a stimulation channel that corresponds to the analysis channel included in the second set of analysis channels.

* * * * *